US011003880B1

(12) United States Patent
Smart et al.

(10) Patent No.: US 11,003,880 B1
(45) Date of Patent: May 11, 2021

(54) METHOD AND SYSTEM FOR CONTACT TRACING

(71) Applicant: Georgetown University, Washington, DC (US)

(72) Inventors: J. C. Smart, Clarksville, MD (US); Timothy E. Denison, Elliott City, MD (US); Edwin Lau, Oakland, CA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 16/985,584

(22) Filed: Aug. 5, 2020

(51) Int. Cl.
*G16H 50/80* (2018.01)
*G06K 7/14* (2006.01)
*G16H 10/40* (2018.01)
*A61B 5/00* (2006.01)
*G07B 5/00* (2006.01)
*H04L 12/18* (2006.01)
*G16H 50/70* (2018.01)
*G06Q 50/26* (2012.01)
*H04W 4/029* (2018.01)
*H04W 4/30* (2018.01)
*H04W 4/021* (2018.01)
(Continued)

(52) U.S. Cl.
CPC .......... *G06K 7/1417* (2013.01); *A61B 5/7282* (2013.01); *A61B 5/746* (2013.01); *G06Q 50/01* (2013.01); *G06Q 50/26* (2013.01); *G06Q 50/265* (2013.01); *G07B 5/00* (2013.01); *G16H 10/40* (2018.01); *G16H 50/70* (2018.01); *G16H 50/80* (2018.01); *H04L 12/1895* (2013.01); *H04W 4/021* (2013.01); *H04W 4/029* (2018.02); *H04W 4/30* (2018.02); *H04W 4/33* (2018.02)

(58) Field of Classification Search
CPC ........ G16H 10/40; G16H 50/70; G16H 50/80; H04W 4/33; H04W 4/029; H04W 4/30
USPC .......................................................... 705/325
See application file for complete search history.

(56) References Cited

U.S. PATENT DOCUMENTS 5,752,017 A 5/1998 Bhargava et al.
5,809,499 A 9/1998 Wong et al.
(Continued)

FOREIGN PATENT DOCUMENTS

WO   WO 2010/120529 A2   10/2010
WO   WO 2010/120529 A3   10/2010

OTHER PUBLICATIONS

David Nield, "How Covid-19 Contact Tracing Works on Your Phone" [online], Jun. 7, 2020 [downloaded Jun. 9, 2020], Wired, 13 pp., Retrieved From the Internet: https://www.wired.com/story/covid-19-contact-tracing-apple-google/.
(Continued)

*Primary Examiner* — Congvan Tran
(74) *Attorney, Agent, or Firm* — Dawn-Marie Bey; Bey & Cotropia PLLC

(57) ABSTRACT

A method and system for contact tracing and alerting anonymously tracks persons within and across digitally modeled areas using registration stations within the area having scannable digital codes which are unique to the area. Upon being alerted to a contagion situation, either from a laboratory or from an area administrator, the system compares electronic visit tickets unique to each person's visit to determine overlap and generates at least one of an exposure event notifications and a contamination event notifications responsive to one or more determinations made by the comparing.

28 Claims, 5 Drawing Sheets

(51) Int. Cl.
H04W 4/33 (2018.01)
G06Q 50/00 (2012.01)

(56) References Cited

U.S. PATENT DOCUMENTS

| | | | |
|---|---|---|---|
| 6,108,787 | A | 8/2000 | Anderson et al. |
| 6,850,252 | B1 | 2/2005 | Hoffberg |
| 6,988,093 | B2 | 1/2006 | Pic et al. |
| 7,603,344 | B2 | 10/2009 | Bousquet et al. |
| 7,649,452 | B2 | 1/2010 | Zilberstein et al. |
| 8,250,235 | B2 | 8/2012 | Harvey et al. |
| 9,996,567 | B2 | 6/2018 | Smart |
| 10,331,644 | B2 | 6/2019 | Smart |
| 10,777,325 | B1 * | 9/2020 | Li .................... G16H 50/80 |
| 10,813,559 | B2 * | 10/2020 | Frank .................... A61B 5/165 |
| 10,845,336 | B2 * | 11/2020 | Abdolahad .......... G01N 27/327 |
| 10,880,303 | B2 * | 12/2020 | Adams, Jr. ............. G06F 21/30 |
| 2002/0112181 | A1 | 8/2002 | Smith |
| 2003/0174723 | A1 | 9/2003 | DeHon et al. |
| 2004/0111639 | A1 | 6/2004 | Schwartz et al. |
| 2004/0133536 | A1 | 7/2004 | Uceda-Sosa |
| 2005/0108526 | A1 | 5/2005 | Robertson |
| 2005/0203892 | A1 | 9/2005 | Wesley et al. |
| 2007/0182983 | A1 | 8/2007 | Wyatt et al. |
| 2008/0072290 | A1 | 3/2008 | Metzer et al. |
| 2008/0263130 | A1 | 10/2008 | Michalowitz et al. |
| 2009/0055934 | A1 | 2/2009 | Jauer |
| 2009/0254572 | A1 | 10/2009 | Redlich et al. |
| 2009/0300002 | A1 | 12/2009 | Thomas et al. |
| 2010/0049687 | A1 | 2/2010 | Patten et al. |
| 2010/0287158 | A1 | 11/2010 | Toledano et al. |
| 2010/0290476 | A1 | 11/2010 | Brindle et al. |
| 2010/0318655 | A1 | 12/2010 | Kajiya |
| 2011/0167110 | A1 | 7/2011 | Hoffberg et al. |
| 2011/0295854 | A1 | 12/2011 | Chiticariu et al. |
| 2012/0131189 | A1 | 5/2012 | Smart et al. |
| 2012/0131530 | A1 | 5/2012 | Moffitt et al. |
| 2012/0330959 | A1 | 12/2012 | Kretz et al. |
| 2013/0111434 | A1 | 5/2013 | Kajiya |
| 2013/0158975 | A1 | 6/2013 | Hwang et al. |
| 2013/0212131 | A1 | 8/2013 | Reddy |
| 2014/0122228 | A1 | 5/2014 | Wical |
| 2020/0253562 | A1 * | 8/2020 | Newberry ............. A61B 5/4845 |
| 2020/0294661 | A1 * | 9/2020 | Aronson ................. G16H 50/20 |
| 2020/0340945 | A1 * | 10/2020 | Abdolahad ......... A61B 10/0051 |
| 2020/0357510 | A1 * | 11/2020 | Bhavani ................. G16H 40/20 |

OTHER PUBLICATIONS

"How Does Contact Tracing Work?," California Connected, californiaconnected.ca.gov, 1 p., downloaded Jun. 9, 2020.
"The Common Gateway Interface" [online], [retrieved on Apr. 26, 2017], 1 p., Retrieved from the Internet: http://web.archive.org/web/20100127161358/http://hoohoo.ncsa.illinois.edu/cgi/.
"HTTP—Hypertext Transfer Protocol Overview" [online], Copyright 1996-2003 [retrieved on Apr. 26, 2017], 6 pp., Retrieved from the Internet: http://www.w3.org/Protocols/.
"RFC 4122—A Universally Unique Identifier (QUID) URN Namespace" [online], Jul. 2005 [retrieved on Apr. 26, 2017], 33 pp., Retrieved From the Internet: http://tools.ieft.org/html/rfc4122.
F. Hirsch, R. Philpott, and E. Maler, Eds. "Security and Privacy Considerations for the OASIS Security Assertion Markup Language (SAML) V2.0," OASIS, Mar. 15, 2005, 33 pp.
Susan Martin, Ph.D., et al., "Forecasting the Break: Building Community and Capacity for Large-Scale, Data-Intensive Research in Forced Migration Studies," A Prosposal to the National Science Foundation, Feb. 2013, 20 pp.
M. A. Thornton and F. R. Chang, "Security Property Checking for Information Processing Circuitry," Georgetown University and Southern Methodist University, 5 pp., Feb. 28, 2014.
"Rapid Information Overlay Technology (RIOT)—A Unifying Approach for Large-Scale Analytics," Raytheon, 15 pp., Oct. 1, 2011.

J. C. Smart, et al., "Privacy Assurance (a.k.a. The "Black Box")—A High-Assurance Method for Sharing and Analysis of Private Information," Georgetown University, et al., 67 pp., Jan. 29, 2014.
S. Adali, et al., "Query Caching and Optimization in Distributed Mediator Systems," Proc. 1996 ACM SIGMOD Conf. on Management of Data, Montreal , Canada, Jun. 1996.
T. Berners-Lee, J. Hendler, O. Lassila, "The Semantic Web," Scientific American, May 2001.
M. Broecheler, A. Pugliese, and V. S. Subrahmanian, "DOGMA: A Disk-Oriented Graph Matching Algorithm for RDF Databases," Proc. 2009 International Semantic Web Conference, Washington, DC, Oct. 2009.
M. Broecheler, A. Pugliese, and V. S. Subrahmanian, "COSI: Cloud Oriented Subgraph Identification in Massive Social Networks," Proc. 2010 Intl. Conf on Advances in Social Networks and Mining (ASONAM-2010), Aug. 2010, Odense, Denmark, pp. 248-255.
M. Broecheler A. Pugliese, and V. S. Subrahmanian, "A Budget-Based Algorithm for Efficient Subgraph Matching on Huge Networks," Proce. 2011 International Conference on Graph Data Management, Hanover, Germany, Apr. 2011, pp. 94-99.
P. Caravelli, Y. Wei, D. Subak, L. Singh, J. Mann, "Understanding Evolving Group Structures in Time-Varying Networks," ASONAM '13, Proceedings of the 2013 IEEE/ACM International Conference on Advances in Social Network Analysis and Mining, pp. 142-148.
R. W. R. Darling and J. R. Norris, "Structure of Large Random Hypergraphs," the Annals of Applied Probability, vol. 15, No. 1A, 2005, pp. 125-152.
D. Dimitrov, L. Singh, J. Mann, "A Process-Centric Data Mining and Visual Analytic Tool for Exploring Complex Social Networks," IDEA '13, Aug. 11, 2013; Chicago, IL, USA.
D. Dimitrov, L. Singh, J. Mann, "Comparison Queries for Uncertain Graphs," Database and Expert Systems Applications, Lecture Notes in Computer Science, vol. 80-56, pp. 124-140, 2013.
A. Pugliese, M. Broecheler, V. S. Subrahmanian, and M. Ovelgonne, "Efficient Multi-View Maintenance Under Insertion in Huge Social Networks," ACM Transactions on the Web, vol. 8, Nr. 2, paper 10 (2014).
J. C. Smart, "The Four-Color Framework—A Reference Architecture for Extreme-Scale Information Sharing and Analysis," Department of Computer Science, Georgetown University, Oct. 2014, http://avsterra.georgetown.edu/tech/4cf.pdf.
J. C. Smart, "Privacy Assurance," International Engagement on Cyber, Georgetown Journal of International Affairs, 2011, http://avesterra.georgetown.edu/tech/privacy_assurance.pdf.
J. C. Smart, "Rapid Information Overlay Technology (RIOT)—A Unifying Approach for Large Scale Analytics," Intelligence and Information Systems, Raytheon Company, Jul. 2010.
J. C. Smart, "Dependency Visualization for Complex System Understanding," Ph.D. Thesis, Universitry of California, Davis, Sep. 1994.
Notification of Transmittal of the International Search Report and the Written Opinion of the International Searching Authority, dated Sep. 3, 2015, for PCT Application No. PCT/US15/33111, 1 p.
International Search Report for PCT Application No. PCT/US15/33111, dated Sep. 3, 2015, 2 pp.
Written Opinion of the International Searching Authority, dated Sep. 3, 2015, for PCT Application No. PCT/US15/33111, 6 pp.
Darlene Storm, "Security in Sexy—Raytheon RIOT Software Tracks People, Predicts Future Behavior," Computerworld, Feb. 11, 2013.
Rosenzweig, Paul S., "Proposals for Implementing the Terrorism Information Awareness System," 2 Geo. J. L. & Pub. Pol'y 169, 2004 (Copyright HeinOnline 2004).
Notification Concerning Transmittal of International Preliminary Report on Patentability (Chapter 1 of the Patent Cooperation Treaty), dated Jun. 6, 2013, PCT/US2011/060332, 1 page.
International Preliminary Report on Patentability, dated May 28, 2013, PCT/US2011/060332, 1 page.
Written Opinion of the International Searching Authority, PCT/US2011/060332, dated Feb. 2, 2012, 4 pages.
DaRosa, Mary, "Data Mining and Data Analysis for Counterterrorism," CSIS Press, Mar. 2004.
Notification of Transmittal of the International Search Report, dated Feb. 2, 2012, PCT/US2011/060332.

(56) References Cited

OTHER PUBLICATIONS

The International Search ,Report, dated Feb. 2, 2012, PCT/US2011/060332.
Written Opinion of the International Searching Authority, dated Feb. 2, 2012, PCT/US2011/060332.
Oracle, Cooperative Server Technology for Transparent Data Sharing, Oracle 7™ Serve SQL Language Reference Manual, Aug. 1993, Part No. A12714-1, pp. 4-288-4-303.
Unidirectional Network from Wikipedia [online], Last Updated Jan. 19, 2016 [retrieved on May 31, 2016], 7 pp., Retrieved from the Internet: en.wikipedia.org/Unidirectional_network.
Douglas W. Jones, Tom C. Bowersox, "Secure Data Export and Auditing Using Data Diodes," Department of Computer Science, The University of Iowa, pp. 1-5, 2006.
Myong H. Kang, Ira S. Moskowitz, Stanley Chincheck, "The Pump: A Decade of Covert Fun," Center for High Assurance Computer Systems, Naval Research Laboratory, 21$^{st}$ Annual Computer Security Applications Conference, 2005, pp. 1-7.
Multilevel Security, from Wikipedia [online], Last Updated May 31, 2016 [retrieved on May 31, 2016]; 11 pp., Retrieved from the Internet: en.wikipedia.org/wiki/Multilevel_security.

* cited by examiner

METHOD AND SYSTEM FOR CONTACT TRACING

CROSS-REFERENCE TO RELATED APPLICATIONS

Cross-reference is made to commonly-owned U.S. Pat. Nos. 9,996,567 and 10,331,644, entitled "PROCESS AND FRAMEWORK FOR FACILITATING DATA SHARING USING A DISTRIBUTED HYPERGRAPH" issued on Jun. 12, 2018 and Jun. 25, 2019, respectively, which claim the benefit of priority to U.S. Provisional Patent Application Ser. No. 62/005,385 entitled ARCHITECTURE FOR EXTREME-SCALE INFORMATION SHARING AND ANALYSIS" filed on May 30, 2014 and U.S. Provisional Patent Application Ser. No. 62/114,883 entitled GLOBAL HYPERGRAPH APPROACH TO REDUCING COMPLEXITY FOR ACCELERATED MULTI-DISCIPLINARY SCIENTIFIC DISCOVERY filed on Feb. 11, 2015 (hereafter "Patent Documents"). The disclosures of the Patent Documents are incorporated herein by reference in their entireties.

BACKGROUND

Field of the Embodiments

The present embodiments are generally directed to methods and systems for tracing contact between individuals and more particularly to a system and method which implement a tracing algorithm based on collected input from identified identities.

Summary of Existing Art

The global pandemic resulting from the spread of the infectious coronavirus disease, COVID-19, has vaulted the need for contact tracing technology to the point of criticality. The most direct way to perform contact tracing is through manual contact tracking which includes interviewing individuals who test positive for COVID-19 (or other infectious diseases) to collect names, locations, events they recently were in physical contact with and attended and then contacting those identified individuals to warn them that they may have been exposed and direct these individuals to testing locations and/or remain in contact through the diseases incubation period to watch for symptom development. A basic description of this process can be found through many online resources such as the California government's COVID-19 page. Many countries and states are in the process of hiring individuals to act as contact tracers to perform the follow-up and monitoring steps described above. As one can readily appreciate, this process is time-consuming and labor intensive. Further, the process relies on the memory and truthfulness of the infected individual to provide information for the contact tracing. A task that is particularly difficult when an individual attends what contact tracers refer to as mass events, where they are potentially in contact with many individuals they do not personally know.

In a limited number of countries, processes referred to as centralized contact tracing may be implemented by the government. Centralized contact tracing systems can run afoul of the privacy laws and regulations when they utilize centralized network-based solutions that collects raw location data on individuals to use in the tracing process. Such information could be collected from mobile phone location tracking, credit card processing information and even CCTV. Using this historical location information, users are able to see when people come into contact. Some countries even make this information publicly available. Such a process is not workable in most jurisdictions where individual privacy is recognized as a right.

Numerous companies are working to implement less intrusive, private and more efficient solutions based on de-centralized tracing, also called distributed contact tracing. One approach currently being explored by countries (and states) is the use of tracking applications (apps) implemented through mobile devices. Ideally, such apps could leverage application programming interface (API) and other technologies and use low-energy wireless technology like Bluetooth signals, to essentially track other mobile devices, e.g., phones, that an individual's mobile device comes into contact with and vice versa. A log is created which includes anonymous identifiers and stores information for 14-days in accordance with current COVID-19 incubation periods. Descriptions of numerous possible proposed app technologies can be found in the article by David Nield, How Covid-19 Contact Tracing Works on Your Phone, WIRED Magazine, Jun. 7, 2020, as well as on the Wikipedia pages for the subject COVID-19 apps, downloaded by the Applicant on Jun. 9, 2020, both of which are incorporated herein by reference in their entireties. One such app, NHSX, developed by the UK's National Health Service (NETS), has been implemented in a very limited testing phase on the Isle of Wright, but is currently under intense scrutiny for perceived weaknesses in data protection policies and plans for broader implementation continue to be pushed back. These technologies require a majority of individuals to install the app in order for them to work and buy-in has not been achieved due to privacy concerns.

Accordingly, there remains a need in the art for an effective solution for providing early warning and automated alerting of infection and/or exposure to contagions, before, throughout, and after pre-pandemic and pandemic situations which support testing, quarantine and self-quarantine processing and maintains a high level of privacy.

SUMMARY OF EMBODIMENTS

In a first exemplary embodiment, a method for contact tracing and alerting, includes: receiving first area data from a first station defining a first area to be monitored, the first area data including a first associated scannable digital code located at the first station; receiving first visit data for a first person from the first station, wherein the first visit data is collected at the station when the first person scans the scannable digital code and further wherein the identity of the first person is anonymous; generating a first electronic visit ticket unique to the first person in response to the first person scanning the first scannable digital code; receiving an indication that the first person has been infected with a contagion; comparing at least the first visit data from the first electronic visit ticket for the infected first person with other electronic visit tickets for other persons and for the first person for the area and for additional areas to determine overlap during a predetermined contagious period for the first person; and generating at least one of an exposure event notification and a contamination event notification responsive to one or more determinations made by the comparing.

In a second exemplary embodiment, a method for contact tracing and alerting, includes: receiving multiple sets of area data digitally defining multiple areas to be monitored, wherein each of the multiple areas includes at least one scanning station, each of the at least one scanning stations having an associated scannable digital code indicating a unique area associated therewith; receiving multiple sets of visit data for multiple persons visiting each of the multiple unique areas from the associated at least one scanning stations, wherein the multiple sets of visit data are collected at the scanning stations when each of the multiple persons scans at least one of the associated scannable digital codes and further wherein each of the multiple sets of visit data is associated with a unique electronic visit ticket generated for each of the multiple persons in response to each of the multiple persons scanning the associated scannable digital code, each of the generated electronic visit tickets indicating a time issued; receiving notification that at least one of the multiple areas is contaminated; comparing unique electronic visit tickets based on the area contamination notification received to determine visits to that area; and generating potential contamination event notifications to any of the multiple persons determined to be visitors of the area during a predetermined potential contamination period, wherein an identity of all of the multiple persons is anonymous.

In a third exemplary embodiment, at least one computer-readable medium storing instructions that, when executed by at least one computing device, perform a method for contact tracing and alerting, includes: receiving first area data from a first station defining a first area to be monitored, the first area data including a first associated scannable digital code located at the first station; receiving first visit data for a first person from the first station, wherein the first visit data is collected at the station when the first person scans the scannable digital code and further wherein the identity of the first person is anonymous; generating a first electronic visit ticket unique to the first person in response to the first person scanning the first scannable digital code; receiving an indication that the first person has been infected with a contagion; comparing at least the first visit data from the first electronic visit ticket for the infected first person with other electronic visit tickets for other persons and for the first person for the area and for additional areas to determine overlap during a predetermined contagious period for the first person; and generating at least one of an exposure event notification and a contamination event notification responsive to one or more determinations made by the comparing.

In a fourth exemplary embodiment, a system for contact tracing and alerting, includes: a plurality of unique, scannable digital codes registered to a plurality of physical stations located at one or more areas to be monitored, the plurality of unique codes existing on one or more computer readable mediums containing instructions for implementing the contact tracing and alerting; a plurality of unique electronic visit tickets generated by instructions programmed in a computer readable medium associated with each of the plurality of physical stations when a mobile device of an individual scans the scannable code at a physical station upon entrance to one of the multiple areas; a network of multiple computer readable mediums programmed to: receive an indication that a person associated with a first unique electronic visit ticket for a first area has been infected with a contagion; compare first visit data from the first unique electronic visit ticket for the infected person with other unique electronic visit tickets for other persons and for the first person for the first area and for additional areas to determine overlap during a predetermined contagious period for the first person; and generate at least one of an exposure event notification and a contamination event notification responsive to one or more determinations made by the comparison

BRIEF SUMMARY OF THE FIGURES

The embodiments will be described below and reference will be made to the drawings, in which.

DETAILED DESCRIPTION

Figure 1A:
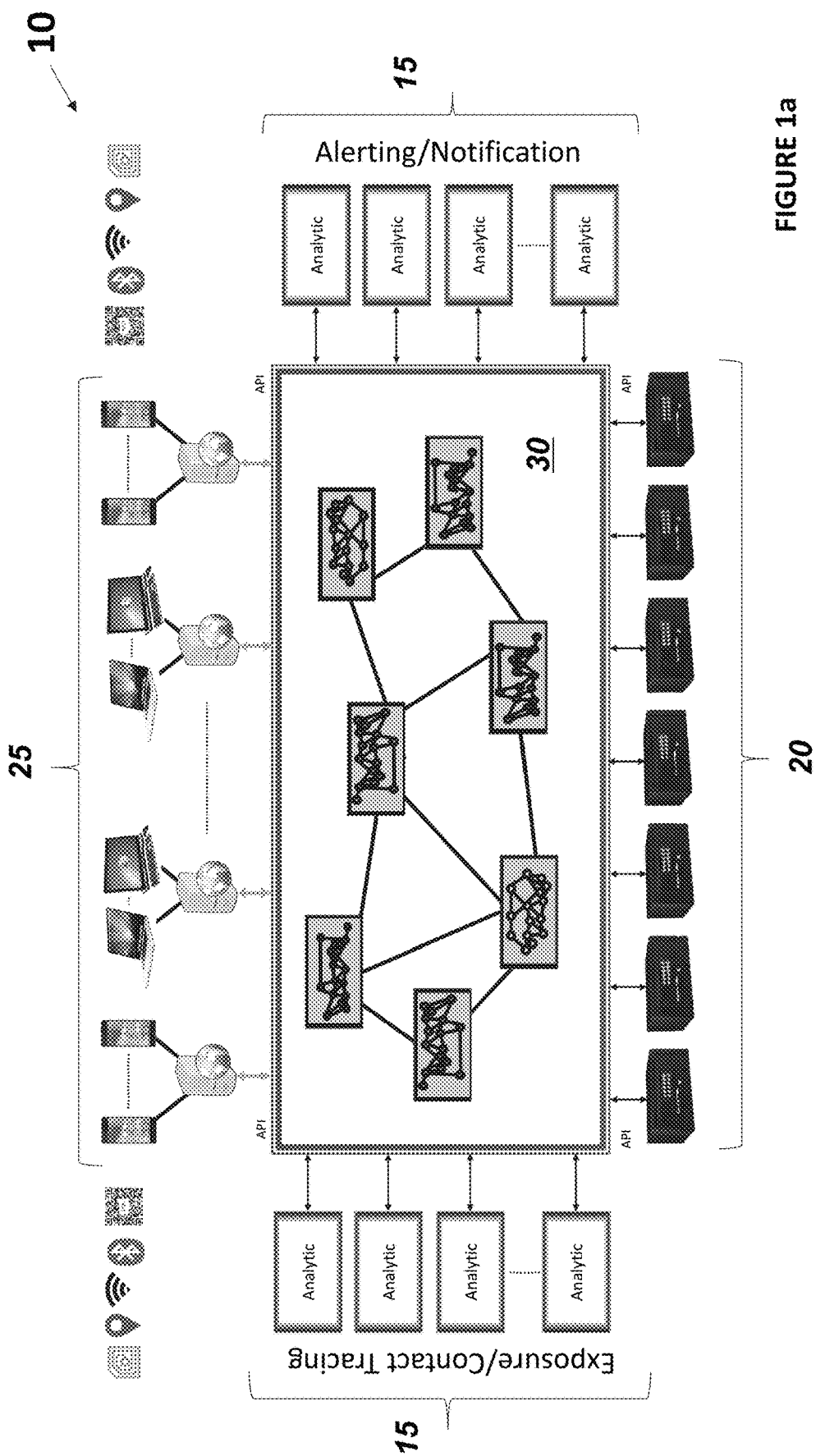
FIGS. 1a and 1b are generalized schematics of the overall framework system architecture (contact tracing system) of the present embodiments.

The embodiments herein leverage the framework disclosed in commonly-owned U.S. Pat. Nos. 9,996,567 and 10,331,644, the contents of which are incorporated herein by reference. The framework architecture 10 is shown in FIG. 1a and includes one or more analytic components 15, one or more data sources, including data appliances (adapters) 20, as well as gateways to cloud appliances 25 which are also sources of data for the algorithm 30, as well as communication devices for receiving alerts. Data may originate from established sensors, detectors and the like. These system components feed and interact with a contact tracing algorithm 30 and each other via API's which may be standardized or customized as needed. The contact tracing algorithm 30 may operate in a distributed fashion across multiple components within the framework architecture 10 (also references herein as "contact tracing system"). Data sources include, but are not limited to, government, healthcare, business, industry, education, telecommunications, travel and individuals.

Figure 1B:
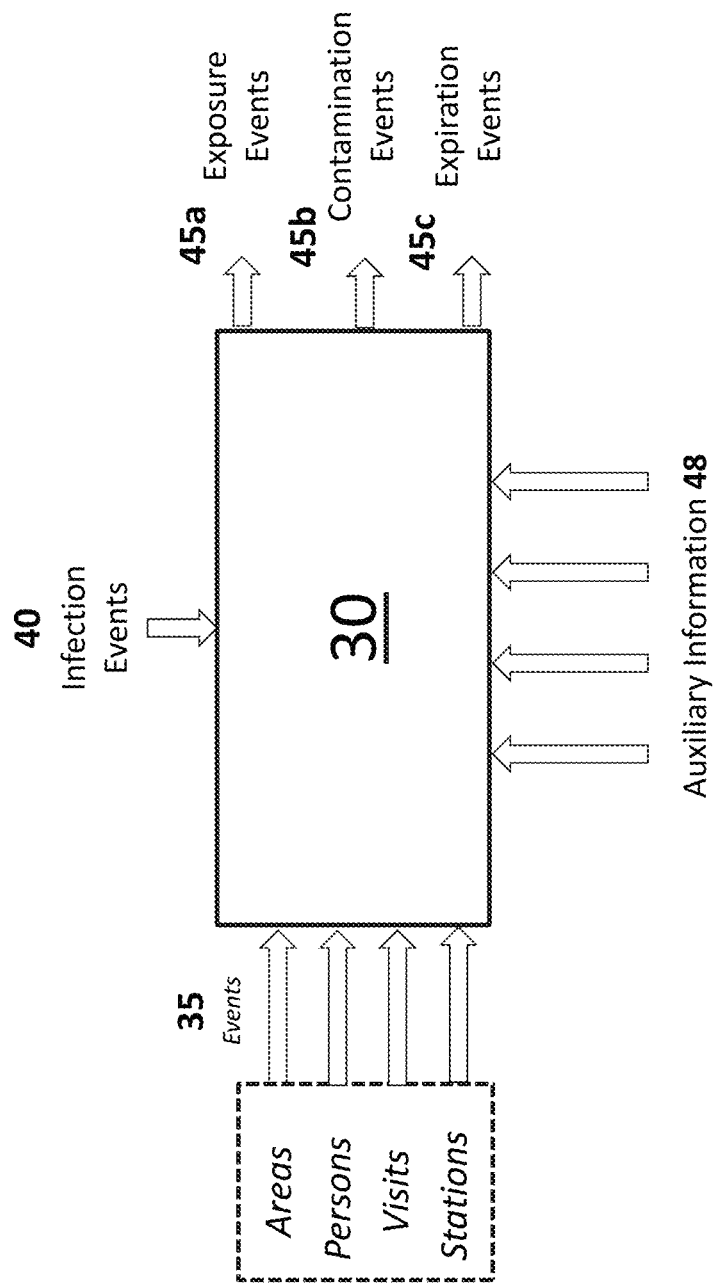

Central to the contact tracing solution of the present embodiments is a contact tracing algorithm 30 that is configured to operate in the framework to perform the contact tracing computations. Referring to FIG. 1b, within the contact tracing domain, data for at least the following entities (constructs) is input to the contact tracing algorithm 30 layer of the framework.

Area, which is an enclosed area, space, or event that is administered by a requirement that entering individuals are subject to a scan process. Administered areas may be either stationary (e.g. rooms, buildings) or mobile (e.g. vehicles, airplanes).

Station, which is a location associated and immediately adjacent to or contained within the Area where a person scan operation is performed.

Person is an anonymous digital representation of a User who visits Areas using their digital device to scan Stations. The anonymous digital representation is assigned to the User as part of an initial Contact Tracing App set-up process.

Visit is when a Person has registered at a Station in an Area.

In addition to these primary entities, the embodiments described below also refer to an individual who is the owner of a mobile digital device which is running the contact tracing algorithm implementation application (hereafter "Contact Tracing App"). An individual becomes a Person for the purposes of the tracing functionality when the individual registers at a Station in an Area to initiate a Visit. Also reference herein are tickets which is a digital identifier issued to a Person at a Station upon entry, exit, or during their Visit to an Area.

In addition to individuals, administrators of Areas and Stations, access and interact with the contact tracing system using mobile and/or stationary processing devices which are programmed to implement the features and functionality of the Contact Tracing App as described herein. As discussed further below, in certain embodiments, individual users of the Contact Tracing App have some level of control regarding their anonymity when implementing features of the Contact Tracing.

Further to FIG. 1b, events 35 regarding changes to Areas, Stations, Persons, and Visits flow into the contact tracing algorithm 30 and infection notification events 40 are received at the contact tracing algorithm 30 as event publications. The contact tracing algorithm 30 uses this information to calculate exposure events related to anonymous Persons represented by tickets, contamination events in Areas, as well as expiration events on Visits, which are outputs 45a, 45b, 45c from the contact tracing algorithm 30. In certain embodiments, auxiliary information 48 such as target capacities of areas, density of people in areas, indoor/outdoor area, area capabilities and air quality (e.g., ventilation, filtration, etc.). may also be provided to the contact tracing algorithm 30 and used in the computations.

Figure 2:
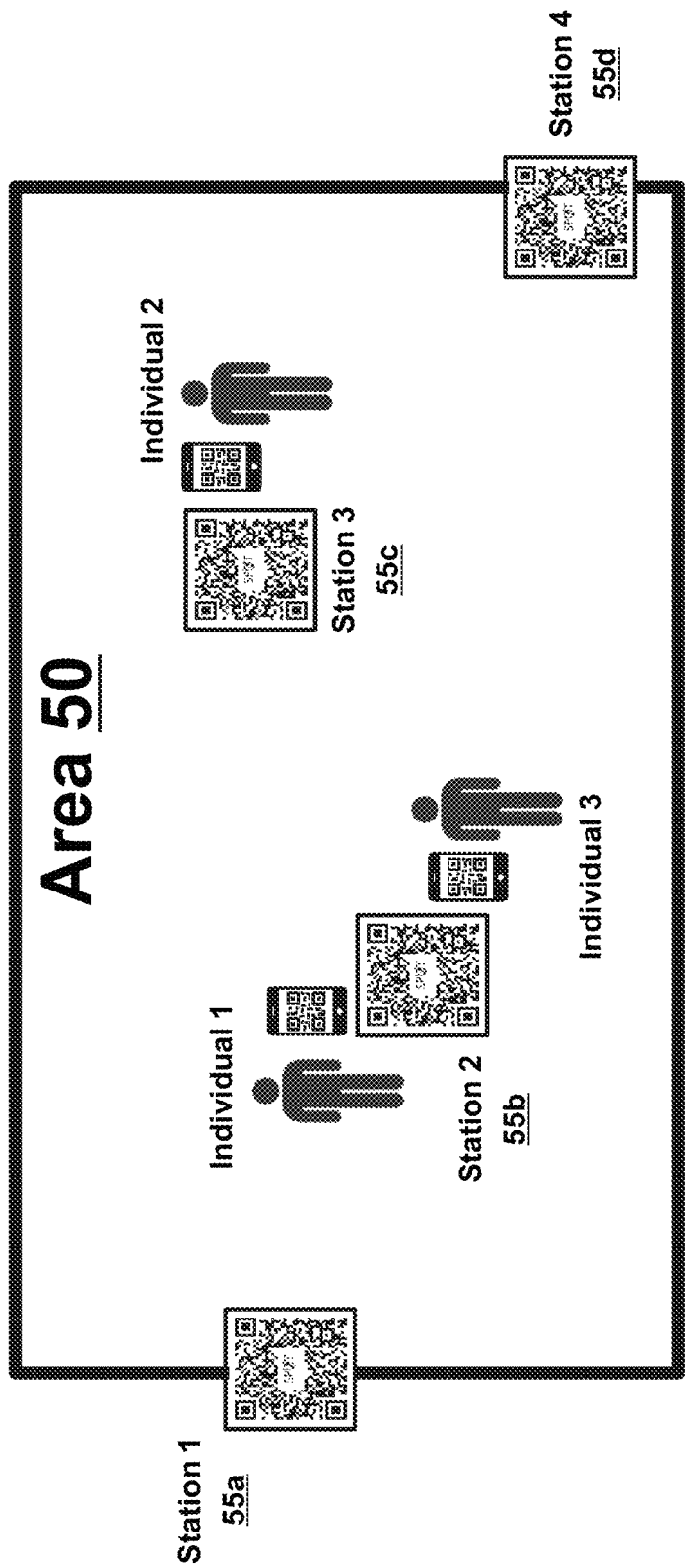
FIG. 2 is a schematic of an Area which is monitored using the contact tracing system in accordance with an embodiment herein.

FIG. 2 presents an exemplary and hypothetical Area 50 with Stations 55a, 55b, 55c and 55d which are identified by a unique code that can be scanned by the Contact Tracing App running on an individual's digital device, e.g., mobile phone. Stations are entities that can be readily created by using a simple mobile or desktop application that allocates and registers a unique digital code, for the designated Area, and registers that Station and its associated Area with the contact tracing system. The unique digital code could be a Quick Response (QR) code, an RFID or other unique digital code capable of being scanned. In the simplified schematic of FIG. 2, Individuals 1 and 3 scanned the Area 50 code at the same station, Station 2 55b, while Individual 2 scanned the Area 50 code at Station 3 55c. As discussed herein, this scanning results in the generation of a unique electronic visit ticket for each Individual which includes at least the Area information, Station information and time of scan information. Within the context of this specification, once the individual scans into the area, they are referenced herein as an anonymous Person for the purposes of the Contact Tracing system and App.

In a preferred embodiment, Stations are configured to allow an individual to enter an Area anonymously as a Person. In an alternative embodiment, a system could require the individual to be identifiable (onymous). Onymous entry may be required in special circumstances as determined by the administrator (owner) of the Area. Stations may be configured with a maximum occupancy, allowing only a limited number of people to be in the Area at one time. Optionally, a Station may be configured to allow the Person to obtain ticketing for additional guests who are accompanying the person on the visit (e.g. close family members or a group of individuals who do not have a device to scan the digital code) collectively associated with a single ticket, but with each counting towards the Area occupancy limit. In addition, Areas may optionally require a Person to obtain a ticket (i.e. scan a Station) both upon entry and exit to an Area.

What qualifies as an Area is limited only by the requirement that entering individuals are subject to a scan process as discussed herein. Accordingly, closed (e.g., buildings, individual rooms within buildings), open (e.g., parks, open air concert venues) and partially closed physical spaces (e.g., stadiums) may all be monitored in accordance with the process and system described herein. As may the physical area around a Person or Persons when the Person declares themselves an Area or station. By declaring the Area around a Person, Visitors to meetings with the Person may be traced (e.g., one-on-one meetings).

For an individual to initiate a Visit to an Area as a Person, the individual must have a mobile device with the Contact Tracing App for scanning the digital code at the Area To register a visit, an individual scans the posted digital code at a Station with their mobile device. This scan results in the generation and receipt of a unique digital Ticket with the time and assigned to both the Person and the Area visited. Where permissible, the Person must indicate additional guests that may be accompanying them into the Area. An acknowledge indicator is immediately displayed on the individual's device if they are permitted to enter, or a denial may be displayed if their entry is prohibited. Reasons to deny entry are controlled by the area manager and may include, for example, the maximum occupancy limit of the area would be exceeded. Alternatively, a denial may be displayed if the individual attempted to enter an Area where the Station requires onymous entry and the individual's device is set to anonymous.

Upon scanning, if a Person is permitted access to an area (the default), they are assigned a ticket to that Area and the time of the visit. Electronically, this results in the individual's mobile device receiving an identifier that references the generated ticket. Tickets are entirely anonymous as the identifier is randomly generated and the ticket record contains no personally identifiable information. The ticket identifier is sent to the contact tracing system 10 and stored with the Area they visited. The contact tracing system 10 cross-references ticket information and alerts Persons who might be impacted.

In a preferred embodiment, when a Person exits an Area, they would "check-out" by scanning the posted digital code with their mobile device and indicating departure. This could occur at the same Station, e.g., in the case of a single entrance/exit system, or at a different Station if an Area has multiple scan Stations. Electronically, this results in an update being sent to the contact tracing system 10 with a ticket check-out time. As such, if a Person checks in and checks out of an Area, the associated Visit ticket will contain times for both check-in and check-out for the Person's Visit to the Area.

In circumstances allowing guests, the Person may be responsible for assuring that their guests were included in their check-out, depending upon how the Area administrator configured the Area. This check-out process, where enabled, can be streamlined as a single scan operation. For Areas configured with check-outs as optional, the system 10 can automatically check-out the Person (and any guests) as determined by the Area's configuration parameters. The "auto" check-out process might occur when the individual's device checks-in at a different Area's Station (thus allowing the contact tracing system 10 to infer that the Person has left the first Area), a pre-configured period of time has elapsed, or the system 10 has other information that it can use to infer or calculate the Person's departure (e.g. an event schedule for the Area, hours of operation for the Area, etc.). For a computed exit, the system 10 adds a predetermined average elapsed time to an entry time for the Person, wherein the predetermined average elapsed time is calculated based on multiple prior visits to the Area by multiple persons.

In an alternative embodiment, GPS tracking may be used to determine when a Person's mobile device has left a predetermined area.

An individual's device may optionally set their device to onymous operation mode. Onymous operation means that the individual has allowed the association of the Person with the individual to become visible to the system during the notification process 10. The primary advantage for onymous operation, regardless of Area requirements, is that an individual can be directly alerted by the system, even when the Contact Tracing App is not running on their device. That is, onymous operation allows individuals to receive alerts via text and/or e-mail message directly. However, even in onymous operation, the only information visible to the system 10 is that which the individual has optionally entered. For example, name, email, telephone, etc. are all optional fields. If the individual has optionally entered personally identifiable information into the Contact Tracing App, then the system 10 could be able to access this information given a ticket identifier. While onymous operation is always optional on the device, some Areas may require that Persons entering must be identifiable (e.g. boarding an aircraft). The individual has the ability to turn 'on' and 'off' onymous operation at their discretion. And at no time are these details about the individual stored with tickets or used during any computation, the onymous details about an individual are only used by the system to authorize entry to designated areas, when required by the area owner, and during the notification process to enhance the notification experience For those Areas which have self-notification enabled, the system 10 will notify, at the area manager's request, based on tickets issued, all Persons who were visitors of an area during an area-owner defined timeframe. For instance, if the administrator of an Area receives a (manual) notification that an exposure incident occurred within their Area, the administrator of the Area can proactively generate an alert using the system 10 for that area using their mobile or desktop application.

In an alternative embodiment, an individual may have the option to self-report a positive test through the Contact Tracing App. This manual entry would initiate the contact tracing algorithm 30 to perform the necessary visit ticket reviews and to generate applicable exposure event and/or contamination event notifications.

Alert information, including the time of occurrence when available (e.g. date of a test), is sent to the system 10 which determines the universe of Tickets of all other Tickets that were issued to Persons for the same Areas during the affected timeframe. The system 10 then automatically publishes notifications to those individuals with tickets that meet the exposure criteria. When an individual's device receives a ticket notification, the Contact Tracing App can use the unique ticket identifier to alert the individual accordingly. As the tickets that are issued to a Person are recorded anonymously, the system 10 will automatically notify Persons with tickets to other Areas where the infected person has visited during the relevant timeframe, and according to appropriate exposure criteria. The process is repeated automatically until all potentially exposed Persons have been notified.

When individuals operate their devices anonymously, i.e., with the Contact Tracing App in anonymous mode, this entire process is performed without the system 10 having access to any of the User's identifiable information. If they have enabled onymous operation (perhaps temporarily as entry into a specific Area required it), then the system 10 would have the ability to notify the User directly (via text message or email) if such User information were available. In either case, however, infection and exposure alerts never contain personally identifiable information which only go to Persons that may be affected.

Testing of individuals and notification of infection is simply a special case of this general structure. That is, a digital code is registered and posted at each testing Station within a testing facility or site, designating each specific Station as an administered Area. The Station for each of these test Areas would be configured with a maximum occupancy of one individual. When a patient arrives to be tested, they familiarly scan the digital code at the test Station with their mobile device Contact Tracing App. Just as with all other Areas, the person's ticket to this testing Station is recorded, again using a unique ticket identifier. Using the Contact Tracing App, the administrator of the testing Station can view the tickets issued at their Station. If the test ultimately yields a positive result, the administrator of the testing services (e.g. an official/professional at the public health organization or the testing laboratory) need simply enter an infection alert for that Ticket, again using the Contact Tracing App on their device, or a desktop application. If the test requires time to process at a testing laboratory, the ticket identifier can be affixed to the patient's test health care record that is transmitted. If a positive determination is made by the testing laboratory, the laboratory, or testing facility, can initiate an alert condition by entering the Station/visit identifiers using their mobile or desktop Contact Tracing App. Alternatively, the unique identifier of the test sample itself can be scanned by the individual and attached to their ticket by the Contact Tracing App. In this case, if the laboratory determines a positive result, they can issue an alert on this sample identifier, which only the patient knows is associated with their ticket. In either case, the contact tracing and alerting notification is then automatically executed by the system 10. If desired and allowed by the public health policy, the entire testing process can occur anonymously with the same alerting process, all performed automatically.

Figure 3:
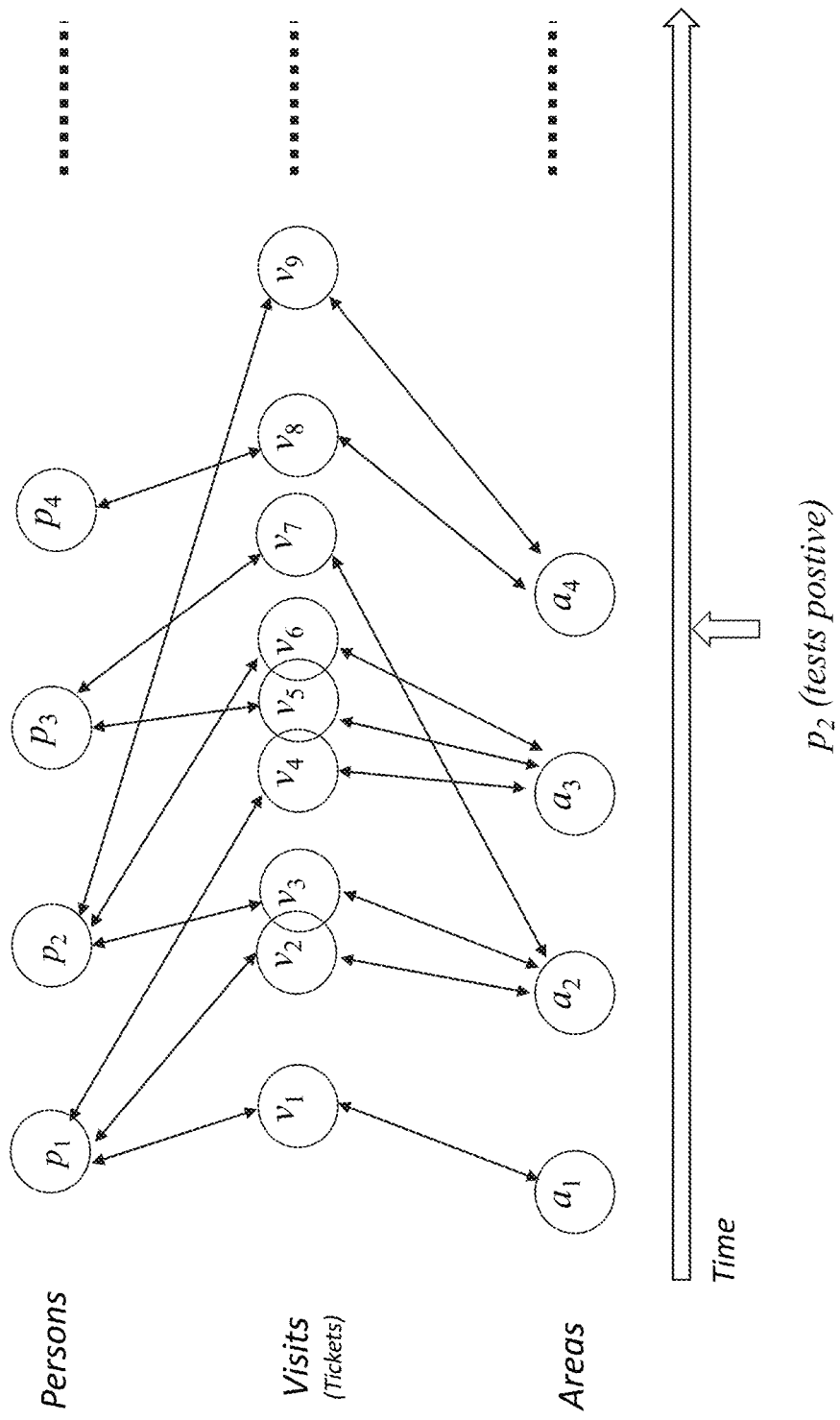
FIG. 3 is a schematic of the organization of data within the contact tracing algorithm in accordance with an embodiment herein.

Referring to FIG. 3, the contact tracing algorithm 30 works internally by building a digital in-memory model of the Area ($a_{1-x}$), Station, Persons ($p_{1-x}$), and Visit ($v_{1-x}$) entities that stream in from the system 10 from Station devices, including Area administrator devices, individual's devices and possibly third-party devices, such as testing laboratories. This model organizes these entities and their relationships according to their time history.

When an infection alert is received, the contact tracing algorithm 30 computes exposure event alerts 45$a$, contamination event alerts 45$b$, and expiration event alerts 45$c$ that are used to automatically notify Users and system administrators. The contact tracing algorithm 30 factors in the latest information that it has regarding the configuration and state of the Areas, Stations, Persons, and Visits. In one embodiment, the contact tracing algorithm 30 is deterministic. In an alternative embodiment, the contact tracing algorithm 30 leverages available auxiliary information 50. A machine learning based approach may be implemented to minimize false positive rates when information is absent, particularly involving visit duration and infection probability.

Figure 4:
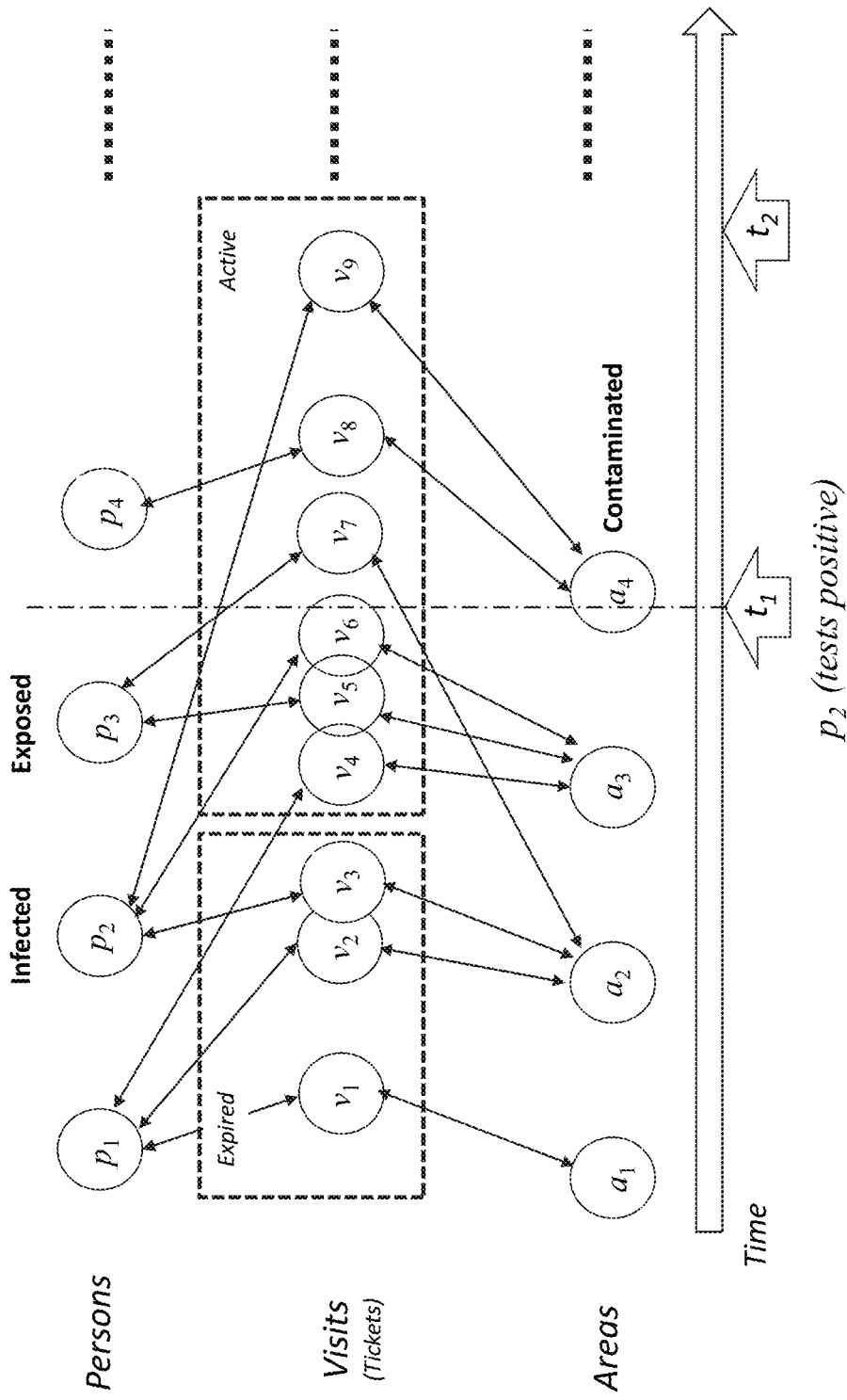
FIG. 4 is a schematic showing an example of a contact tracing exposure/contamination determination the contact tracing algorithm in accordance with an embodiment herein.

An example of the algorithm's operation is shown in FIG. 4, depicting the results generated for an infection alert. In FIG. 4, the system receives notification that Person $p_2$ has been infected at time $t_1$ and determines based on all received entity information that Person $p_3$ may have been exposed based on the overlap between Visits vs and $v_6$ between Persons $p_2$ and $p_3$ in Area $a_3$ during the active time period. And at time $t_2$, the system recognizes that Area $a_4$ is contaminated during the active time period because of the Visit $v_9$ by Persons $p_2$. Accordingly, at time $t_1$, the system 10 sends an exposure event notification to Person $p_3$ and at time $t_2$, the system 10 sends a contamination event notification to Area $a_4$. And once the active period ends for each of the Areas as measured from Person $p_2$ visit time, the system 10 can send notifications of expiration to the Area $a_4$. Receipt of the contamination even notification by an Area could trigger closure and/or cleaning processes in order to limit additional exposure to the contagion by other Persons.

The system 10 automatically purges visit tickets when they are no longer relevant to the contact tracing and exposure identification based on the nature of the contagion's infectious period.

The system and process described herein can provide reliable, large-scale automated contact tracing efficiently, at very low cost and anonymously.

The invention claimed is:

1. A method for contact tracing and alerting, comprising:
    receiving first area data from a first station defining a first area to be monitored, the first area data including a first associated scannable digital code located at the first station;
    receiving first visit data for a first person from the first station, wherein the first visit data is collected at the station when the first person scans the scannable digital code and further wherein the identity of the first person is anonymous;
    generating a first electronic visit ticket unique to the first person in response to the first person scanning the first scannable digital code;
    receiving an indication that the first person has been infected with a contagion;
    comparing at least the first visit data from the first electronic visit ticket for the infected first person with other electronic visit tickets for other persons and for the first person for the area and for additional areas to determine overlap during a predetermined contagious period for the first person; and
    generating at least one of an exposure event notification and a contamination event notification responsive to one or more determinations made by the comparing.

2. The method according to claim 1, further comprising:
    receiving second visit data for a second person from the first station, wherein the second visit data is collected at the first station when the second person scans the first scannable digital code and further wherein the identity of the second person is anonymous;
    generating a second electronic visit ticket unique to the second person in response to the second person scanning the first scannable digital code;
    comparing the first visit data from the first electronic visit ticket for the infected first person with the second electronic visit ticket for the second person;
    determining an overlap between a time the infected first person was in the first area and a time the second person was in the first area; and
    generating an exposure event notification responsive to the determination of an overlap and providing the exposure event notification to the second person.

3. The method according to claim 1, further comprising:
    determining a time for when the first person exits the first area; and
    updating the first electronic visit ticket to indicate the determined duration of the visit.

4. The method according to claim 3, wherein determining the duration of the visit includes receiving updated first visit data from the first station or from a different station in the first area when the first person exits the first area.

5. The method according to claim 3, wherein determining an exit time includes adding a predetermined average elapsed time to an entry time for the first person, wherein the predetermined average elapsed time is calculated based on multiple prior visits to the first area by multiple persons.

6. The method according to claim 3, wherein determining an exit time includes determining that the first person entered a second area.

7. The method according to claim 3, wherein determining the duration of the visit includes receiving duration data specific to an event scheduled for the first area.

8. The method according to claim 1, wherein receiving an indication that the first person has been infected with a contagion includes receiving the indication from a health testing station, wherein the indication is in the form of a health testing station electronic visit ticket generated by the health testing station when the first person visits the health testing station and scans the health testing station scannable digital code and further wherein a positive test result is indicated in the health testing electronic visit ticket using an anonymous laboratory code.

9. A method for contact tracing and alerting, comprising:
    receiving multiple sets of area data digitally defining multiple areas to be monitored, wherein each of the multiple areas includes at least one scanning station, each of the at least one scanning stations having an associated scannable digital code indicating a unique area associated therewith;
    receiving multiple sets of visit data for multiple persons visiting each of the multiple unique areas from the associated at least one scanning stations, wherein the multiple sets of visit data are collected at the scanning stations when each of the multiple persons scans at least one of the associated scannable digital codes and further wherein each of the multiple sets of visit data is associated with a unique electronic visit ticket generated for each of the multiple persons in response to each of the multiple persons scanning the associated scannable digital code, each of the generated electronic visit tickets indicating a time issued;
    receiving notification that at least one of the multiple areas is contaminated;
    comparing unique electronic visit tickets based on the area contamination notification received to determine visits to that area; and
    generating potential contamination event notifications to any of the multiple persons determined to be visitors of the area during a predetermined potential contamination period, wherein an identity of all of the multiple persons is anonymous.

10. The method of claim 9, wherein the notification that at least one of the multiple areas is contaminated is received directly from and administrator of the contaminated area.

11. The method of claim 9, wherein the notification that at least one of the multiple areas is contaminated is determined after receipt from a health testing station of a health testing station electronic visit ticket including a positive test result that is generated by the health testing station when one of the multiple persons visits the health testing station and scans the health testing station scannable digital code and further wherein a positive test result is indicated using an anonymous laboratory code.

12. At least one computer-readable medium storing instructions that, when executed by at least one computing device, perform a method for contact tracing and alerting, comprising:
    receiving first area data from a first station defining a first area to be monitored, the first area data including a first associated scannable digital code located at the first station;

receiving first visit data for a first person from the first station, wherein the first visit data is collected at the station when the first person scans the scannable digital code and further wherein the identity of the first person is anonymous;

generating a first electronic visit ticket unique to the first person in response to the first person scanning the first scannable digital code;

receiving an indication that the first person has been infected with a contagion;

comparing at least the first visit data from the first electronic visit ticket for the infected first person with other electronic visit tickets for other persons and for the first person for the area and for additional areas to determine overlap during a predetermined contagious period for the first person; and generating at least one of an exposure event notification and a contamination event notification responsive to one or more determinations made by the comparing.

13. The at least one computer readable medium according to claim 12 that, when executed by at least one computing device, further comprises:

receiving second visit data for a second person from the first station, wherein the second visit data is collected at the first station when the second person scans the first scannable digital code and further wherein the identity of the second person is anonymous;

generating a second electronic visit ticket unique to the second person in response to the second person scanning the first scannable digital code;

comparing the first visit data from the first electronic visit ticket for the infected first person with the second electronic visit ticket for the second person;

determining an overlap between a time the infected first person was in the first area and a time the second person was in the first area; and generating an exposure event notification responsive to the determination of an overlap and providing the exposure event notification to the second person.

14. The at least one computer readable medium according to claim 12 that, when executed by at least one computing device, further comprises:

determining a time for when the first person exits the first area; and updating the first electronic visit ticket to indicate the determined duration of the visit.

15. The at least one computer readable medium according to claim 14 that, when executed by at least one computing device, further comprises: wherein determining the duration of the visit includes receiving updated first visit data from the first station or from a different station in the first area when the first person exits the first area.

16. The at least one computer readable medium according to claim 14 that, when executed by at least one computing device, further comprises:

wherein determining an exit time includes adding a predetermined average elapsed time to an entry time for the first person, wherein the predetermined average elapsed time is calculated based on multiple prior visits to the first area by multiple persons.

17. The at least one computer readable medium according to claim 14 that, when executed by at least one computing device, further comprises: wherein determining an exit time includes determining that the first person entered a second area.

18. The at least one computer readable medium according to claim 14 that, when executed by at least one computing device, further comprises: wherein determining the duration of the visit includes receiving duration data specific to an event scheduled for the first area.

19. The at least one computer readable medium according to claim 14 that, when executed by at least one computing device, further comprises: wherein receiving an indication that the first person has been infected with a contagion includes receiving the indication from a health testing station, wherein the indication is in the form of a health testing station electronic visit ticket generated by the health testing station when the first person visits the health testing station and scans the health testing station scannable digital code and further wherein a positive test result is indicated in the health testing electronic visit ticket using an anonymous laboratory code.

20. A system for contact tracing and alerting, comprising:

a plurality of unique, scannable digital codes registered to a plurality of physical stations located at one or more areas to be monitored, the plurality of unique codes existing on one or more computer readable mediums containing instructions for implementing the contact tracing and alerting;

a plurality of unique electronic visit tickets generated by instructions programmed in a computer readable medium associated with each of the plurality of physical stations when a mobile device of an individual scans the scannable code at a physical station upon entrance to one of the multiple areas;

a network of multiple computer readable mediums programmed to:

receive an indication that a person associated with a first unique electronic visit ticket for a first area has been infected with a contagion;

compare first visit data from the first unique electronic visit ticket for the infected person with other unique electronic visit tickets for other persons and for the first person for the first area and for additional areas to determine overlap during a predetermined contagious period for the first person; and generate at least one of an exposure event notification and a contamination event notification responsive to one or more determinations made by the comparison.

21. The system of claim 20, wherein the plurality of unique, scannable codes are digital codes scannable by a mobile device.

22. The system according to claim 21, wherein the digital codes are quick response (QR) codes.

23. The system according to claim 20, wherein the network of multiple computer readable mediums is further programmed to determine a time for when the infected person exits the first area; and updating the first unique electronic visit ticket to indicate the determined duration of the visit.

24. The system according to claim 23, wherein the network of multiple computer readable mediums is further programmed to determine the duration of the visit after receiving updated first visit data from the first station or from a different station in the first area when the infected person exits the first area.

25. The system according to claim 23, wherein the network of multiple computer readable mediums is further programmed to determine an exit time by adding a predetermined average elapsed time to an entry time for the infected person, wherein the predetermined average elapsed time is calculated based on multiple prior visits to the first area by multiple persons.

26. The system according to claim 23, wherein the network of multiple computer readable mediums is further programmed to determine an exit time after determining that the first person entered a second area.

27. The system according to claim 23, wherein the network of multiple computer readable mediums is further programmed to determine the duration of the visit after receiving duration data specific to an event scheduled for the first area.

28. The system according to claim 20, wherein receiving an indication that the person has been infected with a contagion includes receiving the indication from a health testing station, wherein the indication is in the form of a health testing station electronic visit ticket generated by the health testing station when the first person visits the health testing station and scans the health testing station scannable digital code and further wherein a positive test result is indicated in the health testing electronic visit ticket using an anonymous laboratory code.

\* \* \* \* \*